United States Patent
He et al.

(10) Patent No.: US 10,253,030 B2
(45) Date of Patent: Apr. 9, 2019

(54) CRYSTAL FORM, PREPARATION METHOD AND INTERMEDIATE OF DIHYDROPYRIDO RING COMPOUND

(71) Applicant: QILU PHARMACEUTICAL CO., LTD., Jinan, Shandong (CN)

(72) Inventors: Haiying He, Shanghai (CN); Kai Zhou, Shanghai (CN); Xiaolin Li, Shanghai (CN); Xiaofei Wang, Shanghai (CN); Dakun Qin, Shanghai (CN); Xingxing Wang, Shanghai (CN); Feifei Yang, Shanghai (CN); Zheng Wang, Shanghai (CN); Zongbin Li, Shanghai (CN)

(73) Assignee: QILU PHARMACEUTICAL CO., LTD., Shandong (CN)

( * ) Notice: Subject to any disclaimer, the term of this patent is extended or adjusted under 35 U.S.C. 154(b) by 0 days.

(21) Appl. No.: 15/772,942

(22) PCT Filed: Nov. 2, 2016

(86) PCT No.: PCT/CN2016/104325
§ 371 (c)(1),
(2) Date: May 2, 2018

(87) PCT Pub. No.: WO2017/076286
PCT Pub. Date: May 11, 2017

(65) Prior Publication Data
US 2018/0312512 A1 Nov. 1, 2018

(30) Foreign Application Priority Data
Nov. 4, 2015 (CN) .......................... 2015 1 0742546

(51) Int. Cl.
*C07D 487/04* (2006.01)
*A61P 31/20* (2006.01)
*C07C 269/06* (2006.01)

(52) U.S. Cl.
CPC ............ *C07D 487/04* (2013.01); *A61P 31/20* (2018.01); *C07C 269/06* (2013.01); *C07B 2200/13* (2013.01)

(58) Field of Classification Search
CPC .................................................. C07D 487/04
See application file for complete search history.

(56) References Cited

U.S. PATENT DOCUMENTS

| 6,503,913 | B1 | 1/2003 | Goldmann et al. |
| 8,168,642 | B2 | 5/2012 | Li et al. |
| 9,403,814 | B2 | 8/2016 | Zhang et al. |
| 9,938,301 | B2 * | 4/2018 | He ....................... A61K 31/519 |
| 2010/0087448 | A1 | 4/2010 | Li et al. |
| 2012/0149695 | A1 | 6/2012 | Li et al. |

FOREIGN PATENT DOCUMENTS

| AU | 5618401 A | 9/2001 |
| CN | 1297449 A | 5/2001 |
| CN | 101104617 A | 1/2008 |
| CN | 103570626 A | 2/2014 |
| CN | 103724339 A | 4/2014 |
| JP | 2002-512244 A | 4/2002 |
| JP | 2009-542729 A | 12/2009 |
| JP | 2012-530726 A | 12/2012 |
| WO | WO-2001/0168641 A1 | 9/2001 |

OTHER PUBLICATIONS

Sep. 24, 2017 International Search Report issued in International Patent Application No. PCT/CN2016/104325.
Sep. 24, 2017 Written Opinion issued in International Patent Application No. PCT/CN2016/104325.
Science, 299 (2003), 893-896.
Biochem. Pharmacol. 66 (2003), 2273-2279.
Protective Groups in Organic Synthesis, Wiley and Sons, 1991.
CN 2015107425469 filed on Nov. 4, 2015 (withdrawn before publication).
May 18, 2018 the First Office Action issued in counterpart Canadian application 3,004,147.
Notification of Reasons for Refusal issued in Japanese application No. 2018-522961 dated Nov. 27, 2018.

* cited by examiner

*Primary Examiner* — Bruck Kifle
(74) *Attorney, Agent, or Firm* — Harness, Dickey & Pierce, P.L.C.

(57) ABSTRACT

Disclosed in the present disclosure are a crystal form of a dihydropyrido ring compound, and preparation method and intermediate thereof.

Compound 1

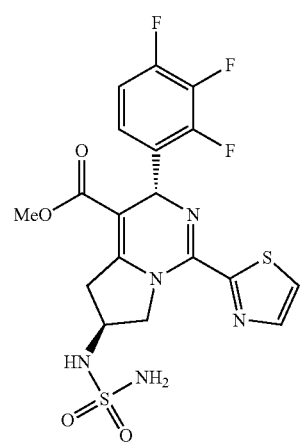

26 Claims, 2 Drawing Sheets

US 10,253,030 B2

CRYSTAL FORM, PREPARATION METHOD AND INTERMEDIATE OF DIHYDROPYRIDO RING COMPOUND

CROSS-REFERENCE TO RELATED APPLICATIONS

This application is a National Stage of International Application No. PCT/CN2016/104325, filed on Nov. 2, 2016, and published in Chinese as WO2017/076286 A1 on May 11, 2017. This application claims the priority to Chinese Patent Application No. 201510742546.9, filed on Nov. 4, 2015. The entire disclosures of the above applications are incorporated herein by reference.

FIELD

The present disclosure relates to a crystal form of a dihydropyrido ring compound, and preparation method and intermediate thereof.

PRIOR ARTS

Hepatitis B virus belongs to Hepadnaviridae. It can cause acute and/or continuous/progressive chronic disease. Hepatitis B virus also causes many other clinical manifestations in pathomorphology, especially chronic liver inflammation, liver cirrhosis and hepatocellular carcinoma. In addition, co-infection with Hepatitis D may have adverse effects in the development of the disease.

Conventional agents licensed for the treatment of chronic hepatitis are interferon and Iamivudine. However, interferon is only moderately active and has high toxicity; although Iamivudine has good activity, its resistance increases rapidly during treatment and often rebounds after treatment was stopped. The $IC_{50}$ value of Iamivudine (3-TC) is 300 nM (*Science*, 299 (2003), 893-896).

Deres et al. reported heteroaryl ring-substituted dihydropyrimidine (HAP) compounds represented by Bay41_4109 and Bay39_5493 which can inhibit HBV replication by preventing the formation of normal nucleocapsid. Bay41_4109 showed better pharmacokinetic parameters in clinical studies (*Science*, 299 (2003), 893-896). Studies on its mechanism of action have shown that the heteroaryl ring-substituted dihydropyrimidine compounds alter the angle among the dimers forming the nucleocapsid by acting with the 113-143 amino acid residues of the core protein, resulting in the formation of unstable swollen nucleocapsids, thus accelerating the degradation of core protein (*Biochem. Pharmacol.* 66 (2003), 2273-2279).

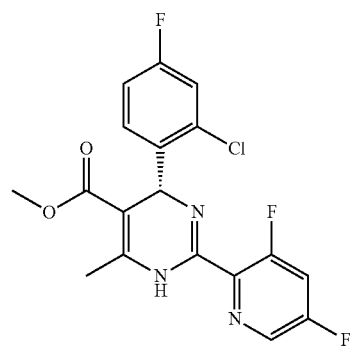

Bay41_4109

There is still a need for new compounds that can be effectively used as antiviral drugs, especially for the treatment and/or prevention of Hepatitis B.

Content of the Present Disclosure

The present disclosure provides a preparation method of Compound 1,

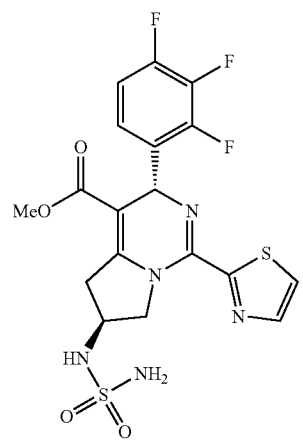

Compound 1 comprising the following steps:

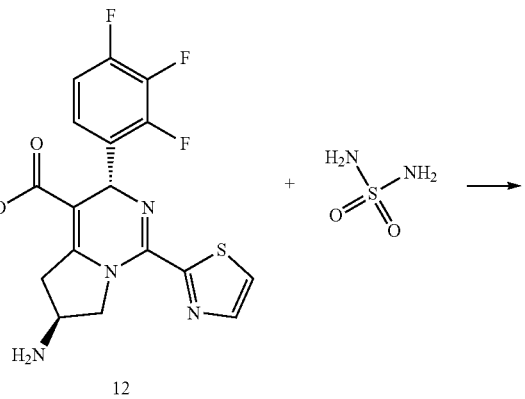

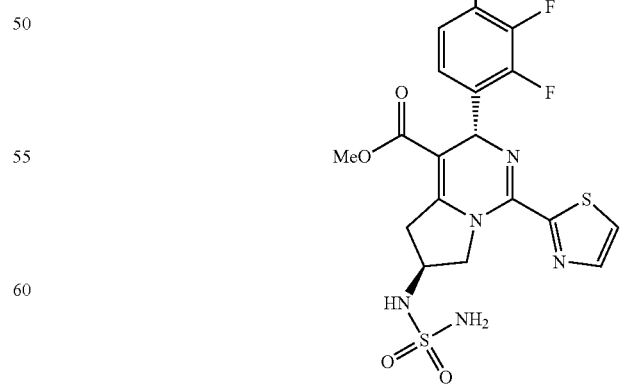

Compound 1 wherein, the reaction step does not require an addition of an organic base or an inorganic base;

the reaction solvent is selected from 1,4-dioxane or tetrahydrofuran;

the molar ratio of Compound 12 to aminosulfonamide is selected from 1:1-20;

the reaction temperature is selected from 60° C. to reflux temperature;

optionally, Compound 1 is purified by recrystallization in a single solvent or a mixed solvent of several solvents selected from the group consisting of dichloromethane, ethyl acetate, isopropyl acetate, n-heptane, n-hexane, cyclohexane and petroleum ether.

In some embodiments of the present disclosure, the molar ratio of Compound 12 to aminosulfonamide is 1:10.

In some embodiments of the present disclosure, Compound 1 is purified by recrystallization in a mixed solvent of dichloromethane or ethyl acetate/n-heptane.

In some embodiments of the present disclosure, in the mixed solvent of ethyl acetate/n-heptane, the volume ratio of ethyl acetate to n-heptane is 0.5:1-2.

In some embodiments of the present disclosure, the above preparation method comprises the following steps,

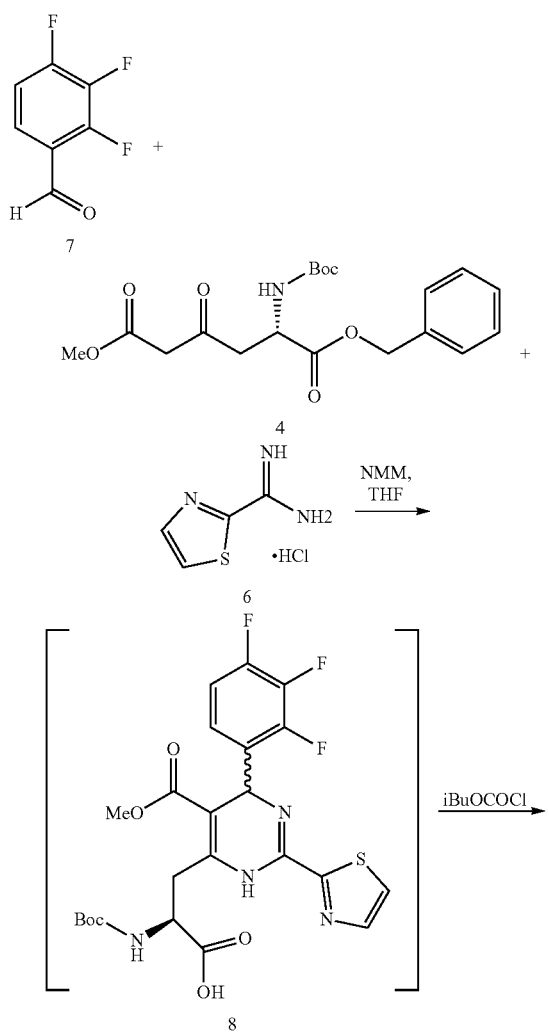

wherein, the molar ratio of NMM to Compound 4 is 1-4:1, preferably 2-3:1;

optionally, Compound 8 is directly added to the next reaction without separation. In some embodiments of the present disclosure, the mixture of Compound 9A and Compound 9B provided by the reaction is separated and purified by recrystallization in a single solvent or a mixed solvent of several solvents selected from the group consisting of ethyl acetate, isopropyl acetate, tetrahydrofuran, dioxane, cyclohexane and n-heptane to give Compound 9A.

In some embodiments of the present disclosure, the molar ratio of NMM to Compound 4 is 2-3:1.

In some embodiments of the present disclosure, the mixture of Compound 9A and Compound 9B provided by the reaction is separated and purified by recrystallization in a mixed solvent of ethyl acetate, tetrahydrofuran and n-heptane to give Compound 9A.

In some embodiments of the present disclosure, in the recrystallization solvent for the mixture of Compound 9A and Compound 9B, the volume ratio of n-heptane, ethyl acetate and tetrahydrofuran is (6-54): (2-18):1.

In some embodiments of the present disclosure, the volume ratio of n-heptane, ethyl acetate and tetrahydrofuran is 18:6:1.

In some embodiments of the present disclosure, the above preparation method comprises the following steps,

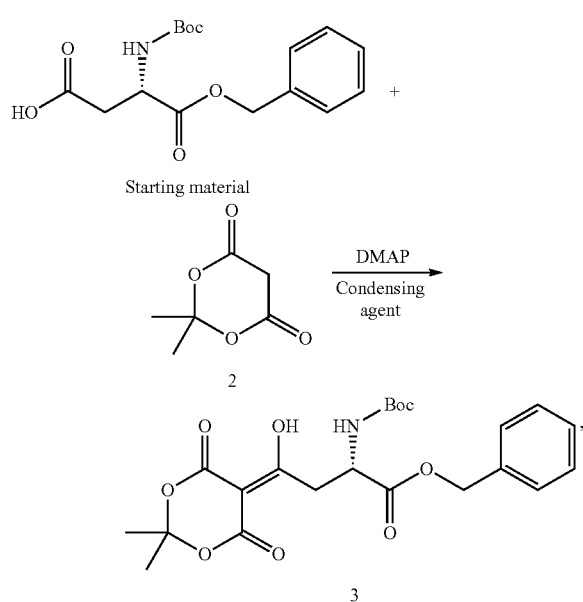

the condensing agent is selected from EDCI, DCC, DIC, DMC, HOBT, HATU, CDI;

the reaction temperature is selected from −20° C. to 10° C.;

optionally, Compound 3 is added directly to the next reaction without separation.

In some embodiments of the present disclosure, the reaction temperature for the preparation of Compound 3 is selected from −10° C. to 0° C.

In some embodiments of the present disclosure, the above preparation method comprises the following steps,

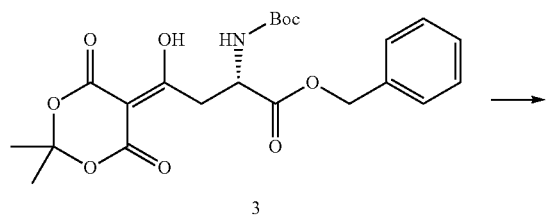

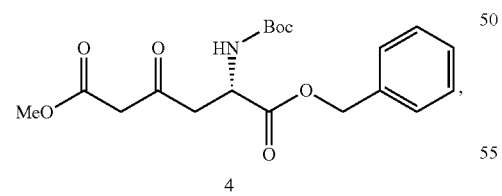

the reaction solvent is a single solvent or a mixed solvent of several solvents selected from the group consisting of methanol, ethanol, isopropanol, n-butanol, t-butanol, tetrahydrofuran, ethyl acetate, toluene and xylene.

In some embodiments of the present disclosure, the reaction solvent for the preparation of Compound 4 is a mixed solvent of toluene and methanol.

In some embodiments of the present disclosure, Compound 4 is purified by stirring crystallization, slurrying or recrystallization in a single solvent or a mixed solvent of several solvents selected from the group consisting of methanol, ethanol, isopropanol, n-butanol, cyclohexane, n-hexane, n-heptane and petroleum ether.

In some embodiments of the present disclosure, Compound 4 is purified by stirring crystallization, slurrying or recrystallization in a mixed solvent selected from the group consisting of ethanol/cyclohexane, ethanol/n-hexane, ethanol/n-heptane or ethanol/petroleum ether.

In some embodiments of the present disclosure, the volume ratio of ethanol to cyclohexane, n-hexane, n-heptane or petroleum ether is selected from 1: 1-3.

In some embodiments of the present disclosure, the volume ratio of ethanol to cyclohexane, n-hexane, n-heptane or petroleum ether is selected from 1: 1-2.

In some embodiments of the present disclosure, the purification solvent for Compound 4 is ethanol/petroleum ether, and the volume ratio of ethanol to petroleum ether is 3:5.

In some embodiments of the present disclosure, Compound 4 is purified by stirring crystallization or slurrying at the temperature of −5° C. to 30° C.

In some embodiments of the present disclosure, Compound 4 is purified by stirring crystallization or slurrying at the temperature of 10° C. to 20° C.

In some embodiments of the present disclosure, the above preparation method also comprises the following steps,

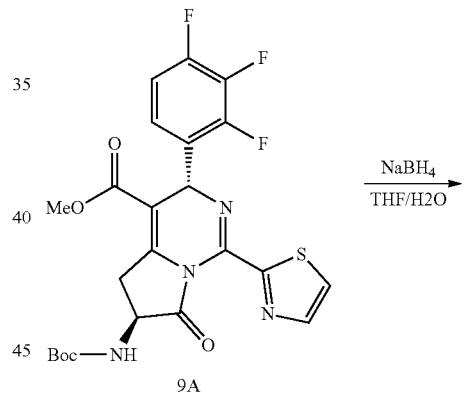

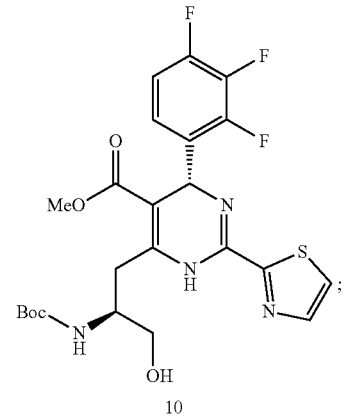

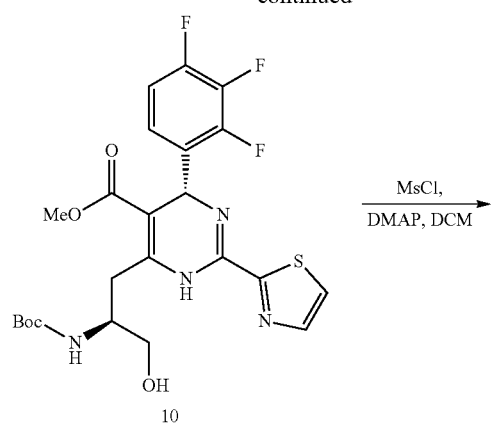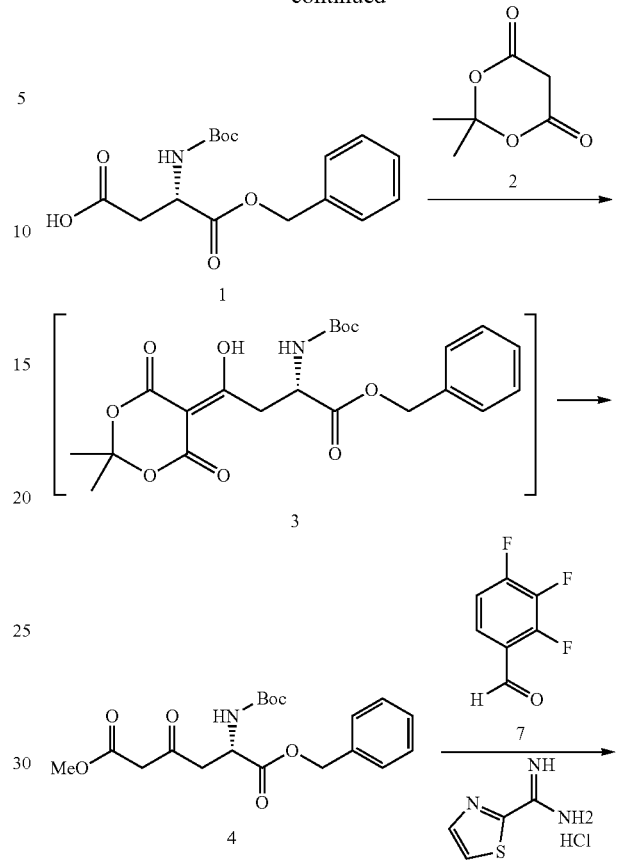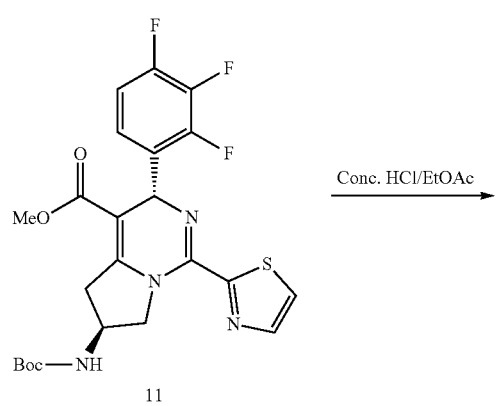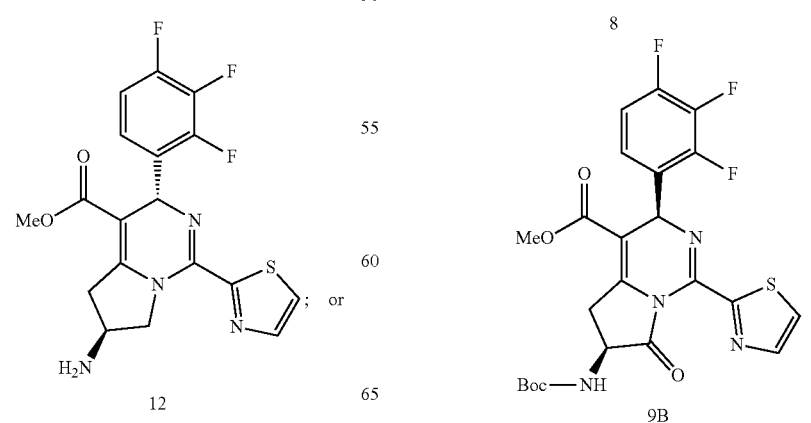

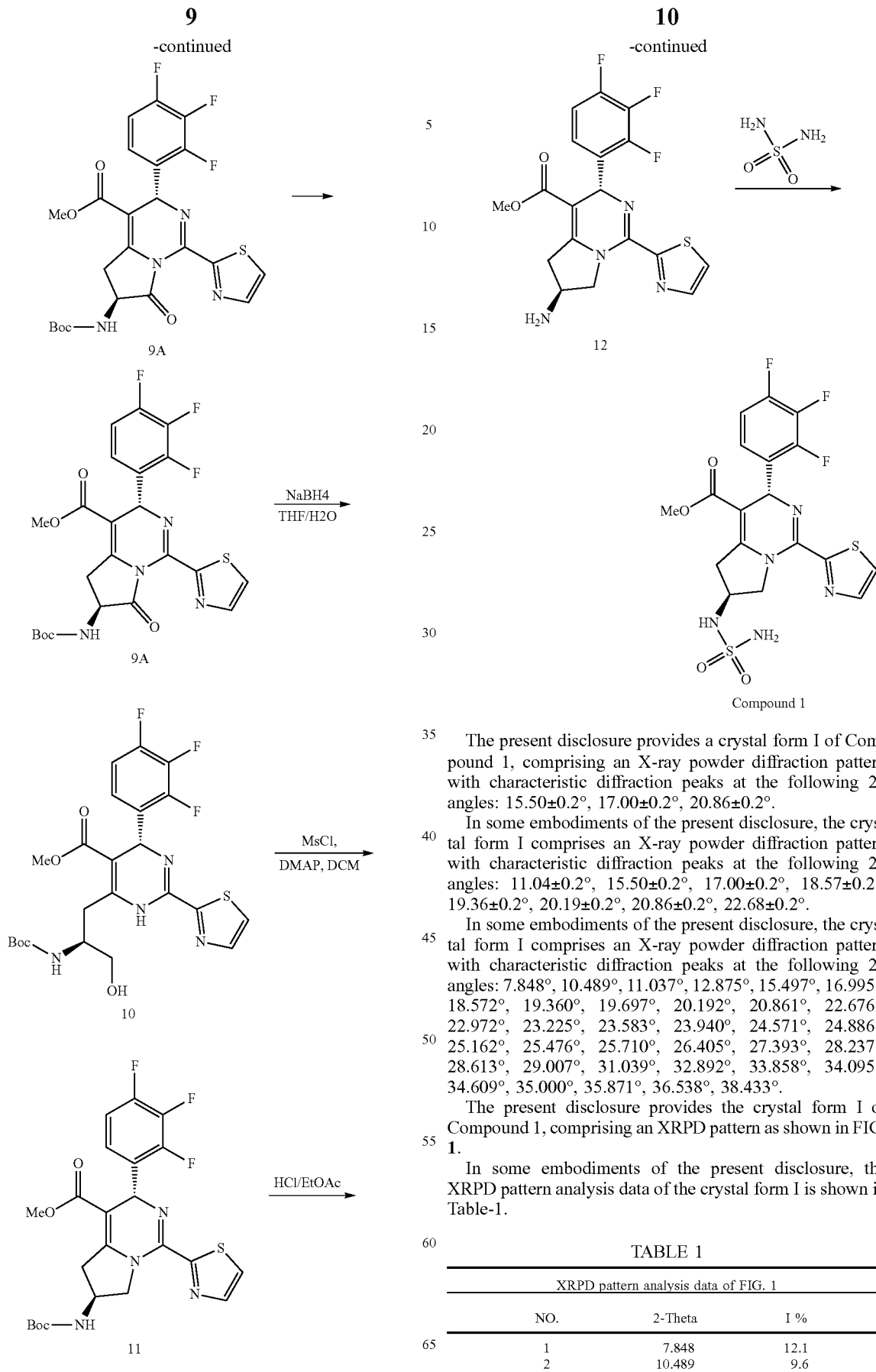

The present disclosure provides a crystal form I of Compound 1, comprising an X-ray powder diffraction pattern with characteristic diffraction peaks at the following 2θ angles: 15.50±0.2°, 17.00±0.2°, 20.86±0.2°.

In some embodiments of the present disclosure, the crystal form I comprises an X-ray powder diffraction pattern with characteristic diffraction peaks at the following 2θ angles: 11.04±0.2°, 15.50±0.2°, 17.00±0.2°, 18.57±0.2°, 19.36±0.2°, 20.19±0.2°, 20.86±0.2°, 22.68±0.2°.

In some embodiments of the present disclosure, the crystal form I comprises an X-ray powder diffraction pattern with characteristic diffraction peaks at the following 2θ angles: 7.848°, 10.489°, 11.037°, 12.875°, 15.497°, 16.995°, 18.572°, 19.360°, 19.697°, 20.192°, 20.861°, 22.676°, 22.972°, 23.225°, 23.583°, 23.940°, 24.571°, 24.886°, 25.162°, 25.476°, 25.710°, 26.405°, 27.393°, 28.237°, 28.613°, 29.007°, 31.039°, 32.892°, 33.858°, 34.095°, 34.609°, 35.000°, 35.871°, 36.538°, 38.433°.

The present disclosure provides the crystal form I of Compound 1, comprising an XRPD pattern as shown in FIG. 1.

In some embodiments of the present disclosure, the XRPD pattern analysis data of the crystal form I is shown in Table-1.

TABLE 1

| XRPD pattern analysis data of FIG. 1 | | |
|---|---|---|
| NO. | 2-Theta | I % |
| 1 | 7.848 | 12.1 |
| 2 | 10.489 | 9.6 |

TABLE 1-continued

XRPD pattern analysis data of FIG. 1

| NO. | 2-Theta | I % |
|---|---|---|
| 3 | 11.037 | 25.4 |
| 4 | 12.875 | 5.3 |
| 5 | 15.497 | 100.0 |
| 6 | 16.995 | 65.0 |
| 7 | 18.572 | 26.0 |
| 8 | 19.360 | 25.8 |
| 9 | 19.697 | 6.2 |
| 10 | 20.192 | 24.8 |
| 11 | 20.861 | 28.4 |
| 12 | 22.676 | 19.0 |
| 13 | 22.972 | 5.8 |
| 14 | 23.225 | 9.9 |
| 15 | 23.583 | 6.6 |
| 16 | 23.940 | 10.6 |
| 17 | 24.571 | 12.3 |
| 18 | 24.886 | 5.0 |
| 19 | 25.162 | 5.0 |
| 20 | 25.476 | 5.8 |
| 21 | 25.710 | 7.8 |
| 22 | 26.405 | 7.2 |
| 23 | 27.393 | 1.9 |
| 24 | 28.237 | 7.7 |
| 25 | 28.613 | 9.4 |
| 26 | 29.007 | 2.9 |
| 27 | 31.039 | 18.5 |
| 28 | 32.892 | 3.6 |
| 29 | 33.858 | 5.2 |
| 30 | 34.095 | 3.2 |
| 31 | 34.609 | 2.9 |
| 32 | 35.000 | 2.9 |
| 33 | 35.871 | 2.2 |
| 34 | 36.538 | 7.1 |
| 35 | 38.433 | 7.3 |

In some embodiments of the present disclosure, the preparation method of the crystal form I comprises the following steps: adding Compound 1 to a mixed solvent of ethyl acetate and petroleum ether for recrystallization, wherein the volume ratio of ethyl acetate to petroleum ether is 1:0.5-2.

In some embodiments of the present disclosure, in the above preparation method of the crystal form I, the volume ratio of ethyl acetate to petroleum ether is 1:1.

In some embodiments of the present disclosure, the preparation method of the crystal form I comprises the following steps: adding Compound 1 to ethyl acetate and heating to reflux for dissolution, then dropwise adding n-heptane, and slowly cooling the mixture to 10° C. to −10° C. for crystallization, wherein the volume ratio of ethyl acetate to n-heptane of 1:0.5-2.

In some embodiments of the present disclosure, in the above preparation method of the crystal form I, the volume ratio of ethyl acetate to n-heptane is 1:1.

The other purpose of the present disclosure is to provide a use of the crystal form I in the preparation of a medicament for treating HBV-related diseases.

Definition and Description

Unless otherwise specified, the following terms and phrases used herein are intended to have the following meanings. A particular phrase or term should not be considered as indefinite or unclear when it is not specifically defined, but should be understood in the ordinary sense. When a trade name appears in this article, it is intended to refer to its corresponding product or its active ingredient.

The intermediate compounds of the present disclosure can be prepared by a variety of synthetic methods well known to those skilled in the art, including the specific embodiments listed below, embodiments obtained through their combination with other chemical synthesis methods, and equivalents well known by those skilled in the art, the preferred embodiments include, but are not limited to, embodiments of the present disclosure.

The chemical reaction of the particular embodiments of the present disclosure is carried out in a suitable solvent which is suitable for the chemical changes of the present disclosure and the reagents and materials thereof. In order to obtain the compounds of the present disclosure, it is sometimes necessary for those skilled in the art to modify or select the synthetic steps or reaction schemes based on the existing embodiments.

An important consideration in any of the synthetic route schemes in the art is the selection of a suitable protecting group for a reactive functional group, such as an amino group in the present disclosure. Greene and Wuts (*Protective Groups In Organic Synthesis*, Wiley and Sons, 1991) are the authority of this field for the trained practitioners. All references cited herein are incorporated in their entirety.

The present disclosure will be specifically described below by way of Examples, which are not intended to limit the present disclosure in any way.

All solvents used in the present disclosure are commercially available and can be used without further purification. The reaction is generally carried out in an anhydrous solvent under an inert atmosphere of nitrogen. Proton NMR data was recorded on a Bruker Avance III 400 (400 MHz) spectrometer with chemical shifts expressed as (ppm) at low field of tetramethylsilane. Mass spectra were determined on an Agilent 1200 Series Plus 6110 (&1956A). The LC/MS or Shimadzu MS contains one DAD: SPD-M20A (LC) and Shimadzu Micromass 2020 detector. The mass spectrometer is equipped with an electrospray ionization source (ESI) operating in positive or negative mode.

The present disclosure adopts the following abbreviations: DCM for dichloromethane; PE for petroleum ether; EA for ethyl acetate; DMF for N, N-dimethylformamide; DMAC for N, N-dimethylacetamide; DMSO for dimethylsulfoxide; EtOAc for ethyl acetate; tol for toluene; THF for tetrahydrofuran; EtOH for ethanol; MeOH for methanol; NMP for N-methylpyrrolidone; 2-METHF for 2-methyltetrahydrofuran; i-PrOH for 2-propanol; Bn for benzyl; Cbz for benzyloxycarbonyl, an amine protecting group; Boc for t-butylcarbonyl, an amine protecting group; Fmoc for carbomethoxycarbonyl, an amine protecting group; Alloc for allyloxycarbonyl, an amine protecting group; Teoc for trimethylsiloxycarbonyl, an amine protecting group; $Boc_2O$ for di-tert-butyl dicarbonate; HCl (g) for hydrogen chloride gas; $H_2SO_4$ for sulfuric acid; HOAc for acetic acid; TFA for trifluoroacetic acid; DIPEA for diisopropylethylamine; DIEA for diisopropylethylamine; NMM for N-methyl morpholine; DBU for 1,8-diazabicycloundec-7-ene; $Et_3N$ for triethylamine; LDA for diisopropylamine lithium; NaHMDS for sodium bis (trimethylsilyl) amide; KHMDS for potassium bis (trimethylsilyl) amide; $LiAlH_4$ for lithium aluminum hydride; t-BuOK for potassium tert-butoxide; $H_2O_2$ for hydrogen peroxide; $NH_4Cl$ for ammonium chloride; $BaSO_4$ for barium sulfate; $CaCO_3$ for calcium carbonate; $SnCl_2$ for stannous chloride; $Zn(BH_4)_2$ for zinc borohydride; $PPh_3$ for triphenylphosphine; HMDS for hexamethyldisilazane; Pd/C for palladium on carbon; $PtO_2$ for platinum dioxide; $Pd(OH)_2$ for palladium hydroxide; $Pd_2(dba)_3$ for tris (dibenzylideneacetone) dipalladium; $Pd(PPh_3)_4$ for tetrakis(triphenylphosphine) palladium; $Pd(dppf)Cl_2$ for 1,1'-bis(diphenylphosphino) ferrocenedichloropalladium; $Pd(OAc)_2$ for palladium acetate; $PdCl_2$ for palladium chloride; CuI for cuprous iodide; CuBr for cuprous bromide; CuCl for cuprous chloride; Cu for copper powder; $Cu_2O$ for cuprous oxide; Xantphos for 4,5-bis (diphenylphosphino) -9,9-dimethylxanthene; Sphos for 2-dicyclohexylphosphino-2',6'-dimethoxybiphenyl; Xphos for 2-dicyclohexylphosphino-2',4',6'-triisopropylbiphenyl; Ruphos for 2-dicyclohexylphosphino-2',6'-diisopropoxy-1,1'-biphenyl; Brettphos for 2-(dicyclohexylphosphino)-3,6-dimethoxy-2'-4'-6'-triisopropyl-1,1'-biphenyl.

Compounds are named manually or with ChemDraw® software, and commercial compounds use the Supplier Directory Name.

X-ray Powder Diffractometer (XRD) Method in the Present Disclosure

Instrument Model: Bruker D8 advance X-ray diffractometer

Test conditions: Detailed XRPD parameters are as follows:

X-ray generator: Cu, kα, (λ=1.54056Å).
Tube voltage: 40 kV, Tube current: 40 mA.
Launch slit: 1 deg.
Limited height slit: 10 mm
Scattering slit: 1 deg.
Accept slit: 0.15 mm
Monochromator: Fixed monochromator
Scanning range: 4-40 deg.
Scanning speed: 10 deg/min Differential Scanning Calorimeter (DSC) Method in the Present Disclosure Instrument Model: TA Q2000 Differential Scanning calorimeter Test conditions: Placing the sample (about 1 mg) in the DSC aluminum pot, testing at 25° C. to 350° C. with a ramp rate of 10° C./min.

Thermal Gravimetric Analyzer (TGA) Method in the Present Disclosure

Instrument Model: TA Q5000IR Thermal Gravimetric Analyzer

Test conditions: Placing the sample (2-5 mg) in the TGA platinum pot, testing at room temperature to 350° C. with a ramp rate of 10° C./min.

TECHNICAL ADVANTAGES

Figure 1:
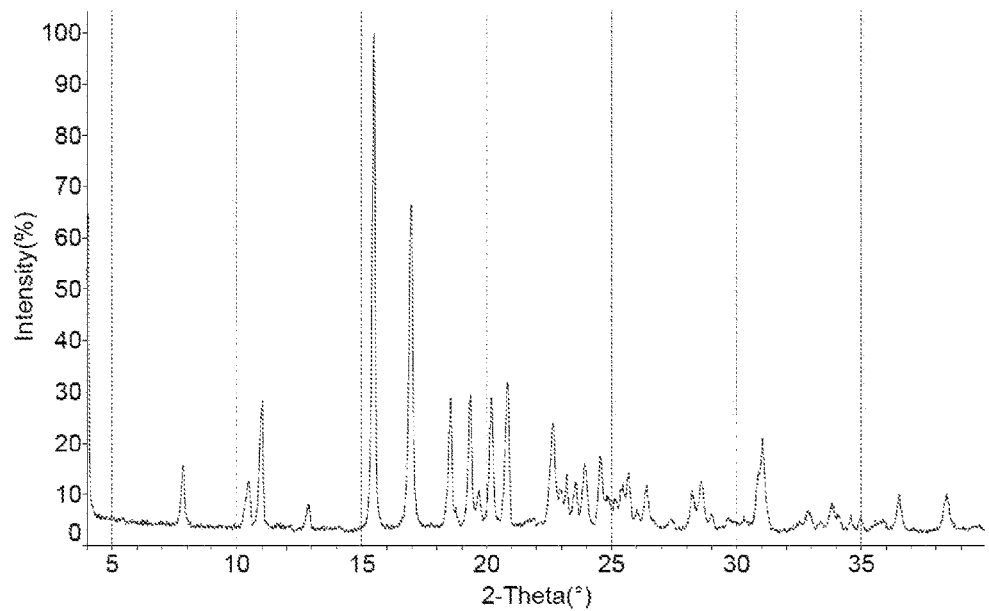
FIG. 1 is the XRPD spectrum of Cu-Kα radiation of the crystal form I.

The advantages of the preparation methods for Compound 1 and the intermediate thereof provided by the present disclosure are as follows: the starting materials are cheap and easy to be obtained; and the disadvantages of large toxicity of reagents, harsh reaction conditions, difficult separation and purification, difficulty of industrialization and the like are overcome.

Specifically:

1) The raw materials of the process of the present disclosure for preparing Compound 1 are conventional or common reagents which are readily available in the market and inexpensive;

2) In the preparation of Compound 4, EDCI, DCC, DIC and the like were used as condensing agents to make the reaction conditions mild. The resulting Compound 4 was purified by stirring crystallization or slurrying with ethanol and a low polar solvent such as petroleum ether or n-heptane, n-hexane or cyclohexane with simple operations and high product purity;

3) In the preparation of Compound 8, Compound 4, Compound 6 and Compound 7 were used as starting materials to synthesize Compound 8 with mild reaction conditions and high yield. Compound 8 can be directly put into the next step without any separation, and the operations were simple.

4) The mixture of Compound 9A and Compound 9B obtained by the reaction was recrystallized from a mixed solvent of ethyl acetate, tetrahydrofuran and n-heptane. Compound 9A can be directly obtained with a purity of more than 95% and De greater than 96%.

5) In the preparation steps of Compound 1, about 10 equivalents of aminosulfonamide and Compound 12 were reacted under reflux using dioxane as a solvent, without adding an inorganic or organic base, the obtained product was clean, and the post-treatment was easy and simple.

6) The crystal form I of Compound 1 is stable I and has a promising prospect for medicine use.

Therefore, the present disclosure has high industrial application and economic value in the preparation of Compound 1 and the intermediates thereof.

DETAILED DESCRIPTION OF THE PREFERRED EMBODIMENT

For a better understanding of the contents of the present disclosure, the following examples further illustrate the present disclosure, but the present disclosure is not limited thereto.

EXAMPLE 1

Preparation of Crude Compound 1

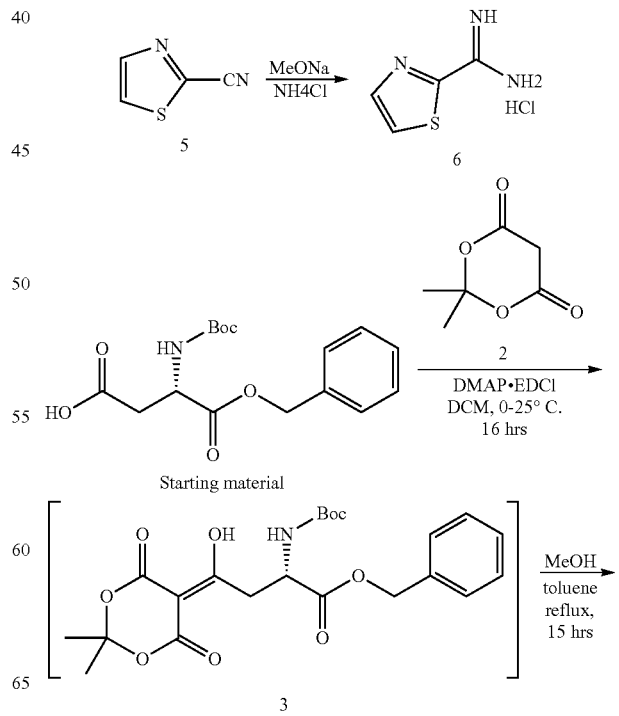

15
-continued
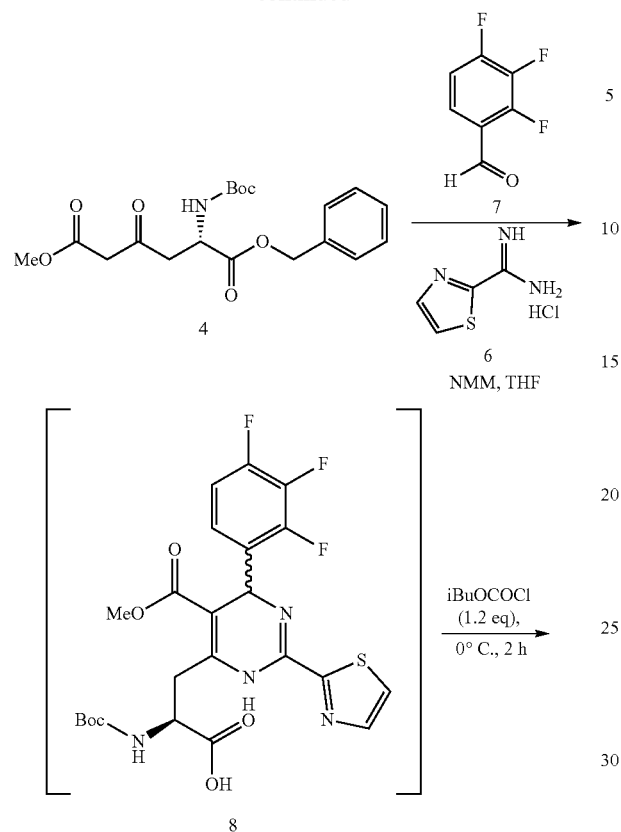
16
-continued
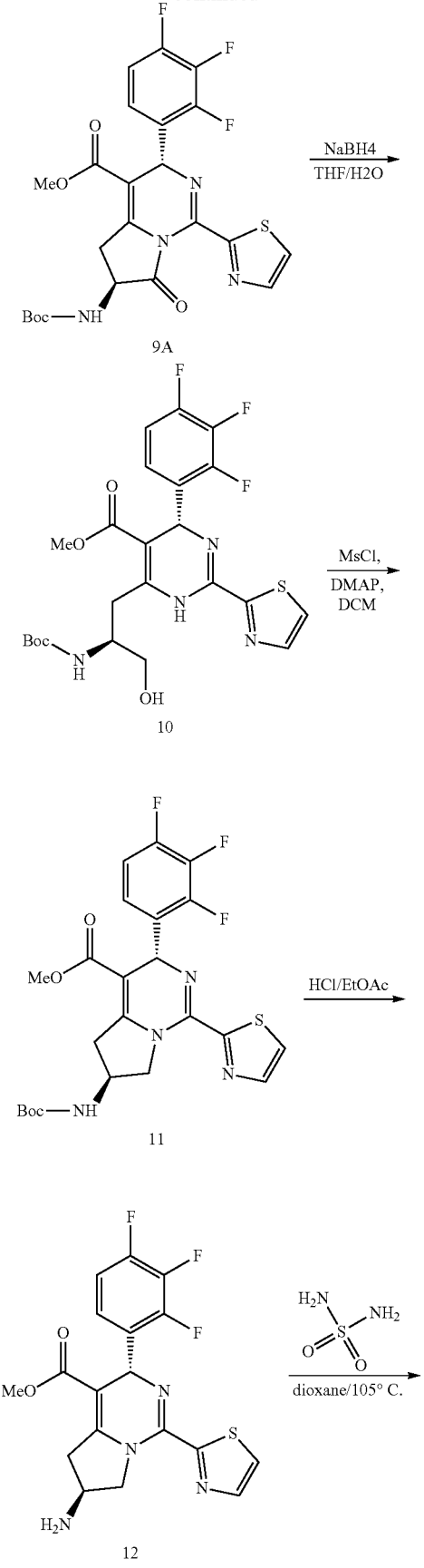

-continued

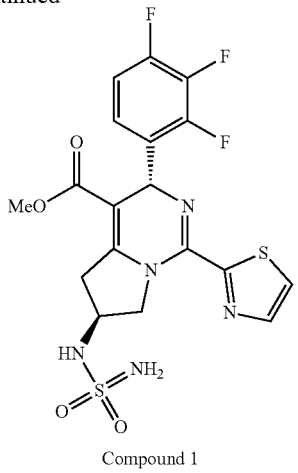

Compound 1

Step 1: Preparation of Compound 4

DCM (12 L) was added into a 50 L reaction kettle, and the starting material (5.00 kg, 15.46 mol) was added, and DMAP (2.83 kg, 23.20 mol) was added, and the mixture was stirred for 10 min. Compound 2 (2.23 kg, 15.46 mol) was added and the temperature of the kettle was cooled to 0° C. EDCI (4.45 kg, 23.20 mol) was dissolved in DCM (20 L) in batches to form a suspension, and then slowly added dropwise to the kettle, and the internal temperature was controlled below 0° C. during the dropping process. Upon the completion of the dropwise addition, the reaction solution was stirred at 0° C. for 16 hours, and then sampled for detection. TLC (PE:EtOAc=1:1) and LCMS detection showed the disappearance of raw materials, indicating that the reaction was completed. The reaction solution was washed with saturated NaHCO$_3$ solution (20 L*2). No DMAP was detected by TLC (PE:EtOAc=0:1) and disappearance of DMAP was confirmed by LCMS. The reaction solution was washed with saturated NaCl solution (15 L) once, concentrated under reduced pressure and spun dry, then added with toluene (3 L) and further concentrated under reduced pressure to give Compound 3. The separated weight was 6.95 kg, the separated yield was 87.7% and the purity was 85%.

$^1$H NMR (400 MHz, CHLOROFORM-d) ppm 1.42 (s, 8 H) 1.65-1.76 (m, 5 H) 3.54-3.72 (m, 2 H) 4.85 (d, J=6.02 Hz, 1 H) 5.07-5.25 (m, 2 H) 5.35 (d, J=8.28 Hz, 1 H) 7.29-7.40 (m, 5 H)

LCMS: m/z: 472.1 [M+Na$^+$]

Anhydrous toluene (20 L) was added into a 50 L reaction kettle, and Compound 3 (6.95 kg, 15.46 mol) was added. Under mechanical stirring, anhydrous MeOH (6.26 L, 154.6 mol) was added. The reaction solution was stirred for 16 h with the internal temperature controlled at 70° C., and then sampled for detection. TLC (PE:EtOAc=1:1) and LCMS detection showed the reaction was completed. The reaction solution was concentrated under reduced pressure to give a reddish brown viscous liquid. The crude product was dissolved in 6 L EtOH and 10 L petroleum ether. The solution was stirred at 13° C. for 30 minutes and a white solid was precipitated. The mixture was stirred for 2 hours, allowed to stand overnight and filtered. The solid was washed with petroleum ether (5 L) for three times and air dried to give a white product (4.2 kg, 11.07 mol). The filtrate was cooled to −11° C. and filtered to give a white product (600 g, 1.58 mol). The total separated weight was 4.8 kg, the separated yield after the two steps was 81.7%, and the purity was 98%.

$^1$H NMR (400 MHz, CHLOROFORM-d) ppm 1.43 (s, 9 H) 3.07-3.16 (m, 1 H) 3.22-3.33 (m, 1 H) 3.44 (s, 2 H) 3.72 (s, 3 H) 4.51-4.62 (m, 1 H) 5.16 (s, 2 H) 5.48 (d, J=8.03 Hz, 1 H) 7.29-7.40 (m, 5 H)

LCMS: m/z: 402.1 [M+Na$^+$]

Step 2: Preparation of Compound 6

MeOH (12 L) was added into a 50 L reaction kettle, and Compound 5 (2200 g, 20.00 mol, 1 eq) was added, and NaOMe (54 g, 1 mol, 0.05 eq) was added and the mixture was stirred at 10° C. for 0.5 h. The reaction mixture was sampled for detection, TLC (PE:EtOAc=2:1) showed the disappearance of the raw materials and the generation of intermediates. NH$_4$Cl (1296 g, 24.00 mol, 1.2 eq) was added and the mixture was stirred at 65° C. for 16 h. The reaction mixture was sampled for detection, TLC (PE:EtOAc=2:1) showed the disappearance of the intermediates, indicating that the reaction was completed. The reaction mixture was filtered to give solid NH$_4$Cl (210 g), and the filtrate was dried to give the crude product. The crude product was slurried with EtOAc (20 L) for 2 h and filtered to obtain the product Compound 6 (3200 g) with a purity of 98%. The effective content of NMR measured by Q-NMR was 95%. The separated yield was 93%.

$^1$H NMR (400 MHz, DMSO-d$_6$) ppm 8.26 (d, J=2.76 Hz, 1 H) 8.38 (d, J=3.01 Hz, 1 H) 9.81 (br. s., 1H)

LCMS: m/z: 127.9 [M+H$^+$]

Step 3: Preparation of Compound 9A

Compound 4 (1140 g, 3 mol) and anhydrous THF (7.5 L) were added to a 30 L jacketed reaction flask and stirred. Compound 6 (566 g, 3.45 mol), Compound 7 (502 g, 1.1 mol) and NMM (760 g, 7.5 mol) were added. The reaction was refluxed (60° C.) for 20 h. The content of the intermediate carboxylic acid was monitored by HPLC and the temperature was cooled to 5-10° C. The isobutyl chloroformate (492 g, 3.6 mol, dissolved in 500 mL THF) was added dropwise and reacted at 5-10° C. for 1 h. TLC and HPLC showed that the intermediate carboxylic acid of the reaction was reacted completely. The reaction was quenched by the addition of H$_2$O (3 L), and extracted with EtOAc (9 L), and the organic solvent was washed once with H$_2$O (3 L) and concentrated to give 2.2 kg of mother liquor. The mother liquor was dissolved in EtOAc (3 L), THF (500 mL) was added, n-heptane (about 9 L) was slowly added dropwise and the mixture was stirred at 15° C. overnight with a solid precipitated, and filtered to give a crude solid with a purity of 95%, De=85%. Recrystallization of the crude product: The solid was dissolved in THF/EtOAc (100 g in 500/500 mL) at 50° C., added dropwise with n-heptane (1 L) and stirred for 1 h, then gradually cooled to 25° C. and stirred overnight, filtered to give Compound 9A as a white solid (500 g, purity: 96%, De>96%, yield: 27%).

$^1$H NMR (400 MHz, CHLOROFORM-d) ppm 1.46 (s, 9 H) 3.11 (dd, J=17.82, 8.03 Hz, 1 H) 3.70 (s, 3 H) 3.86-4.03 (m, 1 H) 4.46 (d, J=7.78 Hz, 1 H) 5.30 (d, J=6.27 Hz, 1 H) 6.02 (s, 1 H) 6.89-7.00 (m, 1 H) 7.01-7.12 (m, 1 H) 7.49 (d, J=3.26 Hz, 1 H) 7.90 (d, J=3.01 Hz, 1 H)

LCMS: m/z: 523.1 [M+H$^+$]

Step 4: Preparation of Compound 10

200 mL of H$_2$O was added into a 10 L reaction flask, and NaBH$_4$ (39.2 g, 1.03 mol) was added to dissolve. Compound 9 (270.0 g, 0.52 mol) was added with 4.0 L of THF to dissolve at 0° C., and slowly added dropwise to the reaction flask. The mixture was reacted for 3 h with the temperature controlled at 0-5° C. Sampling detection showed that the reaction was completed. The reaction mixture was added with 750 mL of HCl (1 mol/L) with the pH adjusted to 7. The reaction mixture was concentrated to give the crude product. The crude product was added with 200 mL of water and extracted with ethyl acetate (500 mL*3). The organic phases were combined, dried over $Na_2SO_4$, and concentrated to give 299 g of crude product with a purity of 97.23%, separated yield>100% (crude), an effective content of 90% and a yield of 96%.

$^1$H NMR (400 MHz, DMSO-$d_6$) ppm 1.14 (s, 9 H) 2.61-2.69 (m, 1 H) 3.38 (br. s., 2H) 3.52-3.59 (m, 4 H) 3.84-3.94 (m, 1 H) 4.81 (t, J=5.65 Hz, 1 H) 5.86 (s, 1 H) 6.40 (d, J=9.54 Hz, 1 H) 7.15-7.25 (m, 2 H) 7.94 (d, J=3.26 Hz, 1 H) 8.01 (d, J=3.01 Hz, 1 H) 9.71 (s, 1 H)

LCMS: m/z: 527.1 [M+H$^+$]

Step 5: Preparation of Compound 11

Compound 10 (269.0 g, 0.51 mol) was added to a 5 L reaction flask and 1.2 L of dichloromethane was added to dissolve, then DMAP (187.4 g, 1.53 mol) was added, and the mixture was stirred for 10 min with the internal temperature cooled to 0° C. A solution of methanesulfonyl chloride (118.09 g, 1.03 mol) in DCM (50 mL) was added dropwise with the internal temperature controlled during the dropwise addition. After the addition was completed, the mixture was reacted under stirring at 0° C. for 20 min, and then at 35° C. for 16 h. Sampling detection showed that the reaction was completed. 1 mol/L HCl (500 mL) was added to the reaction mixture to adjust pH=2-3. The reaction mixture was added with 500 mL of water and extracted with dichloromethane (700 mL*3), and the organic phases were combined. Almost no DMAP was detected in the organic phase, and no target product was detected in the aqueous phase. Then the organic phase was added with 2 mol/L HCl (50 mL) and washed with saturated NaCl (500 mL*2). Almost no DMAP was detected in the organic phase, and the aqueous phase was extracted with dichloromethane (100 mL*3). The combined organic phases were washed with 1M $NaHCO_3$ (300 mL*2), dried over anhydrous $Na_2SO_4$, and concentrated to give 270 g of a yellow solid (separated weight 270 g, separated yield 85.7%, purity 88.56%).

$^1$H NMR (400 MHz, DMSO-$d_6$) ppm 1.38 (s, 9 H) 3.01 (dd, J=17.82, 6.27 Hz, 1 H) 3.35 (dd, J=17.82, 7.53 Hz, 1 H) 3.53 (s, 3 H) 4.06-4.29 (m, 2 H) 4.40 (dd, J=11.04, 6.78 Hz, 1 H) 5.89 (s, 1 H) 7.21-7.27 (m, 2 H) 7.39 (d, J=6.02 Hz, 1 H) 7.89 (d, J=3.26 Hz, 1 H) 7.96 (d, J=3.26 Hz, 1 H)

LCMS: m/z: 509.2 [M+H$^+$]

Step 6: Preparation of Compound 12

Compound 11 (1.1 kg, 2.1 mol, weight content: 97.14% by weight), ethyl acetate (9.9 kg) and concentrated hydrochloric acid (0.87 kg) were added to a 30 L kettle. The mixture was stirred at 25° C. for 3 hours, sampling detection showed that the reaction was completed. 4.4 kg of water was added and the mixture was extracted and separated. The ethyl acetate phase was discarded. The aqueous phase was washed twice with 6.82 kg of dichloromethane, respectively, separated and the dichloromethane phase was discarded. The aqueous phase was further added with 13.25 kg of dichloromethane and 1.19 L of methanol. The mixture was stirred and cooled to 5° C., and about 4.4 kg of 3N sodium hydroxide was gradually added to adjust the pH to 13 (about 20 minutes). The mixture was separated and the organic phase was collected. The aqueous phase was extracted once with a mixed solvent of 9.71 kg of dichloromethane and 0.58 kg of methanol (10/1). The organic phase was dried to give 0.85 kg of crude product (weight content: 94.19%).

$^1$H NMR (400 MHz, DMSO-$d_6$) ppm 1.84 (br. s., 2 H) 2.84 (dd, J=17.57, 6.02 Hz, 1 H) 3.26 (dd, J=17.57, 6.78 Hz, 1 H) 3.55 (s, 3 H) 3.63 (m, J=6.15 Hz, 1 H) 4.00 (dd, J=10.92, 5.65 Hz, 1 H) 4.29 (dd, J=11.04, 6.27 Hz, 1 H) 5.90 (s, 1 H) 7.14-7.31 (m, 2 H) 7.89 (d, J=3.26 Hz, 1 H) 7.97 (d, J=3.26 Hz, 1 H)

LCMS: m/z: 409.1 [M+H$^+$]

Step 7: Preparation of Compound 1

Compound 12 (0.82 kg, 1.89 mol, weight content: 94.19%), 1,4-dioxane (8.2 L) and aminosulfonamide (1.89 kg, 2.35 mol) were sequentially added to a 30 L reaction kettle and purged with nitrogen. The mixture was reacted under reflux for 2 hours. Sampling detection showed that the reaction was almost completed. The reaction solution was spun dry, added with 4.4 kg of ethyl acetate and washed with 12.3 kg of tap water once. The organic phase was added with 6.5 kg of dichloromethane, washed with deionized water (3*12.3 kg) for three times and concentrated to dryness to give crude Compound 1.

EXAMPLE 2

Preparation of the Crystal Form I of Compound 1

The crude product of Example 1 was dissolved with 4.76 kg of dichloromethane under reflux. The solution was cooled by program to −30° C. at the rate of 10° C./0.5 h, and kept at −20° C. for 60 h. A large amount of solid was precipitated and filtered, and the resulting solid was beaten with 2.87 kg of dichloromethane, and filtered to give 790 g of solid. The solid was totally dissolved in 1.58 L of ethyl acetate under reflux, then added dropwise with 1.58 L of n-heptane was added, cooled to 500° C. and stirred until a large amount of solid appeared, then cooled by program (to −10° C. in 100 minutes) and kept at −10° C. for 10 hours. The mixture was filtered, and the resulting solid was washed with a mixed solvent of 0.79 L of ethyl acetate and 0.79 L of n-heptane, and dried in a vacuum oven to give 0.61 kg of the crystal form I of Compound 1 with a purity of 98.5%.

$^1$H NMR (400 MHz, DMSO-$d_6$) ppm 3.07 (dd, J=17.69, 6.90 Hz, 1 H) 3.48 (dd, J=17.82, 7.53 Hz, 1 H) 3.55 (s, 3 H) 4.10 (m, J=6.88 Hz, 1 H) 4.20 (dd, J=11.29, 6.27 Hz, 1 H) 4.51 (dd, J=11.29, 6.78 Hz, 1 H) 5.91 (s, 1 H) 6.76 (s, 2 H) 7.17 (d, J=7.28 Hz, 1 H) 7.22-7.29 (m, 2 H) 7.89 (d, J=3.26 Hz, 1 H) 7.98 (d, J=3.26 Hz, 1 H)

LCMS: m/z: 488.1 [M+H$^+$].

X-ray detection analysis: It was not easy to grow single crystal on Compound 1. To confirm the absolute configuration of Compound 1, Compound 12 was reacted with methanesulfonyl chloride to give Compound 14, and single crystal was grown on Compound 14, the route is as follows,

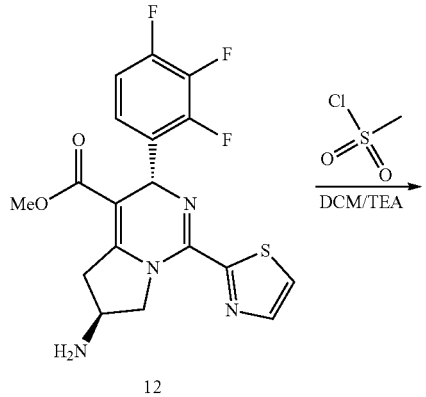

12

-continued

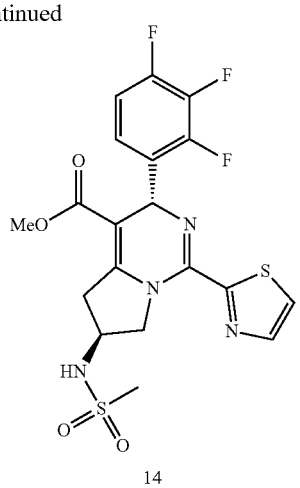

14

Figure 4:
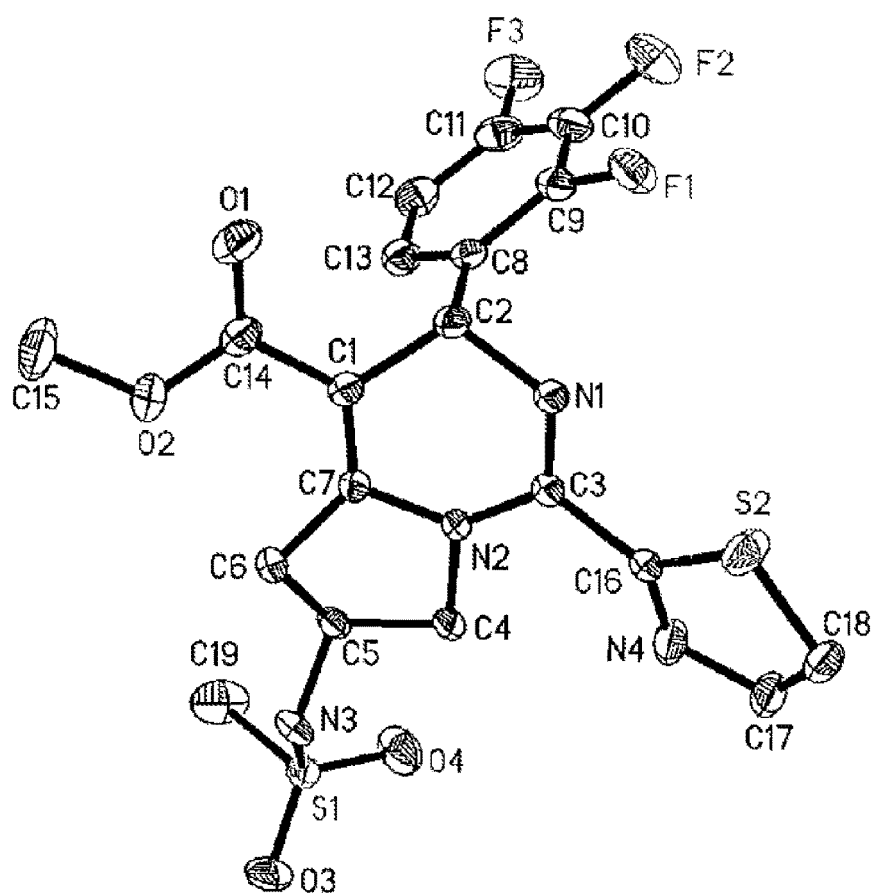
FIG. 4 is the three-dimensional structure ellipsoid diagram of the single molecule of Compound 14.

The substitution reaction occurred on N, and the basicity of TEA used was weak. No inversion occurred in the configuration of the two chiral carbons in Compound 12. Thus, the configuration of the two chiral carbons in Compound 1 was consistent with the configuration of the two chiral carbons in Compound 14. The absolute configuration of Compound 1 can also be determined from the single crystal data of Compound 14. X-Ray for Compound 14 is shown in FIG. 4.

EXAMPLE 3

Preparation of the Crystal Form I of Compound 1

The crude product of Compound 1 obtained in Example 1 was purified by silica gel column. The mobile phase was dichloromethane/methanol=100:1. The resulting product was purified twice by recrystallization in a mixed solvent of ethyl acetate/petroleum ether (1:1 by volume) to give the crystal form I of Compound 1.

qPCR Assay for HBV In Vitro Test

1 Experimental Purpose:

The HBV DNA content in HepG2.2.15 cells was detected by real-time qPCR assay, and the $EC_{50}$ values of the compounds were used as indicators to evaluate the inhibitory effect of the compounds on HBV.

2 Experimental Materials:

2.1 Cell Line: HepG2.2.15 Cells

HepG2.2.15 cell culture medium (DMEM/F12, Invitrogen-11330057; 10% serum, Invitrogen-10099141; 100 units/ml penicillin and 10 μg/ml streptomycin, Invitrogen-15140122; 1% nonessential amino acids, Invitrogen-11140076; 2 mM L-GLUTAMINE, Invitrogen-25030081; 300 μg/ml Geneticin, Invitrogen-10131027

2.2 Reagents:

Trypsin (Invitrogen-25300062)

DPBS (Hyclone-SH30028.01B)

DMSO (Sigma-D2650-100ML)

High-throughput DNA Purification Kit (QIAamp 96 DNA Blood Kit, Qiagen-51162)

Quantitative FastStart Universal Probe Master (FastStart Universal Probe Master, Roche-04914058001)

2.3 Supplies and Equipments:

96-well cell culture plate (Corning-3599)

$CO_2$ Incubator (HERA-CELL-240)

Optical sealing film (ABI-4311971)

Quantitative PCR 96-well plate (Applied Biosystems-4306737)

Fluorescence quantitative PCR instrument (Applied Biosystems-7500 real time PCR system)

1. Experimental Steps and Methods:

3.1 HepG2.2.15 cells ($4 \times 10^4$ cells/well) were seeded in a 96-well plate and incubated at 37° C. under 5% CO 2 overnight.

3.2 On the second day, the compound was diluted into a total of 8 concentrations with 3-fold gradient dilution. Different concentrations of the compound were added to the culture wells, in duplicate. The final concentration of DMSO in the culture medium was 1%. 1 μM GLS4 was used as 100% inhibition control; 1% DMSO was used as 0% inhibition control.

3.3 On the fifth day, the fresh culture medium containing the compound was replaced.

3.4 On the eighth day, the culture medium in the culture wells was collected and DNA was extracted using a high-throughput DNA purification kit (Qiagen-51162). Refer to the product manual for the specific procedure.

3.5 The preparation of PCR reaction solution was as shown in Table 1:

TABLE 1

| Preparation of PCR reaction solution | | |
|---|---|---|
| Item | Required volume for preparation of 1 well (μL) | Required volume for preparation of 80 wells (μL) |
| Quantitative FastStart Universal Probe Master | 12.5 | 1000 |
| Upstream primer (10 μmol) | 1 | 80 |
| Downstream primer (10 μmol) | 1 | 80 |
| Probe (10 μmol) | 0.5 | 40 |

Upstream primer sequence: GTGTCTGCGGCGTTTTATCA

Downstream primer sequence: GACAAACGGGCAACATACCTT

Probe sequence: 5 '+ FAM + CCTCTKCATCCTGCTGCTATGCCTCATC + TAMRA-3'

3.1 15 μl of reaction mixture was added to each well of a 96-well PCR plate, then 10 μl of sample DNA or standard of HBV DNA to each well.

3.2 PCR reaction conditions: heating at 95° C. for 10 minutes; then denaturing at 95° C. for 15 seconds, extension at 60° C. for 1 minute, a total of 40 cycles.

3.3 Data Analysis:

3.8.1 Calculation of the percent inhibition: % Inh.=[1−(DNA copy number in sample−DNA copy number in 1 μM of GLS4)/(DNA copy number in DMSO control−DNA copy number in 1 μM of GLS4).

3.8.2 Calculation of $EC_{50}$: The compound's concentration for 50% of inhibition ($EC_{50}$) value on HBV was calculated using GraphPad Prism software.

4 Experimental Results

The experimental results are shown in Table-3:

TABLE 3

$EC_{50}$ test results of qPCR assay

| Sample | Concentration for 50% of inhibition ($EC_{50}$) value on HBV |
|---|---|
| Compound 1 | A |

Definition of biological activity: A: $EC_{50} \le 100$ nM.

Conclusion: Compound 1 has a significant inhibitory effect on HBV DNA.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are to be regarded as a departure from the disclosure, and all such modifications are intended to be included within the scope of the disclosure.

What is claimed is:

1. The crystal form I of Compound 1, comprising an X-ray powder diffraction pattern with characteristic diffraction peaks at the following 2θ angles: 15.50 ±0.2°, 17.00±0.2°, 20.86±0.2°;

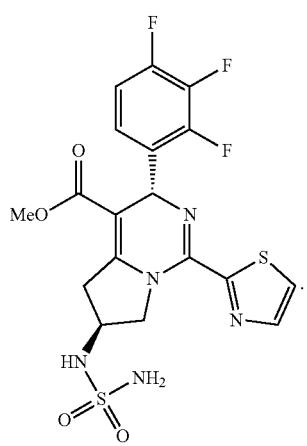

Compound 1

2. The crystal form I according to claim 1, comprising an X-ray powder diffraction pattern with characteristic diffraction peaks at the following 2θ angles: 11.04±0.2°, 15.50±0.2°, 17.00±0.2°, 18.57±0.2°, 19.36±0.2°, 20.19±0.2°, 20.86±0.2°, 22.68±0.2°.

3. The crystal form I of Compound 1, comprising an X-ray powder diffraction pattern with characteristic diffraction peaks at the following 2θ angles: 7.848°, 10.489°, 11.037°, 12.875°, 15.497°, 16.995°, 18.572°, 19.360°, 19.697°, 20.192°, 20.861°, 22.676°, 22.972°, 23.225°, 23.583°, 23.940°, 24.571°, 24.886°, 25.162°, 25.476°, 25.710°, 26.405°, 27.393°, 28.237°, 28.613°, 29.007°, 31.039°, 32.892°, 33.858°, 34.095°, 34.609°, 35.000°, 35.871°, 36.538°, 38.433°;

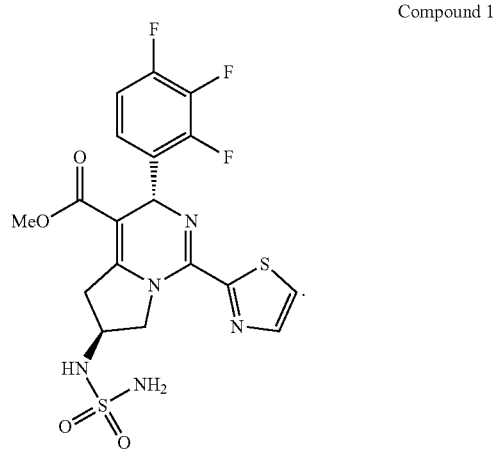

Compound 1

4. The crystal form I of Compound 1, comprising an XRPD pattern as shown in FIG. 1,

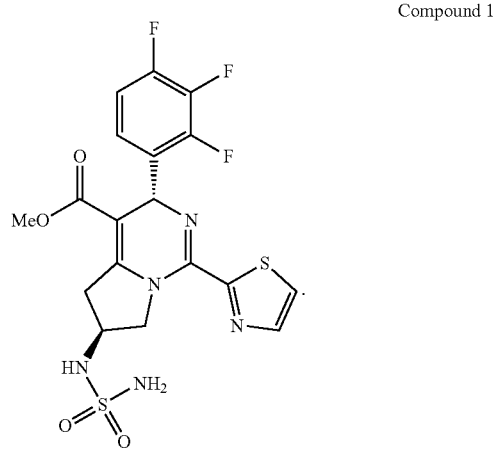 [SMILES: COC(=O)C1=C2C[C@H](NS(N)(=O)=O)CN2C(c2nccs2)=N[C@H]1c1ccc(F)c(F)c1F]

Compound 1

Figure 2:
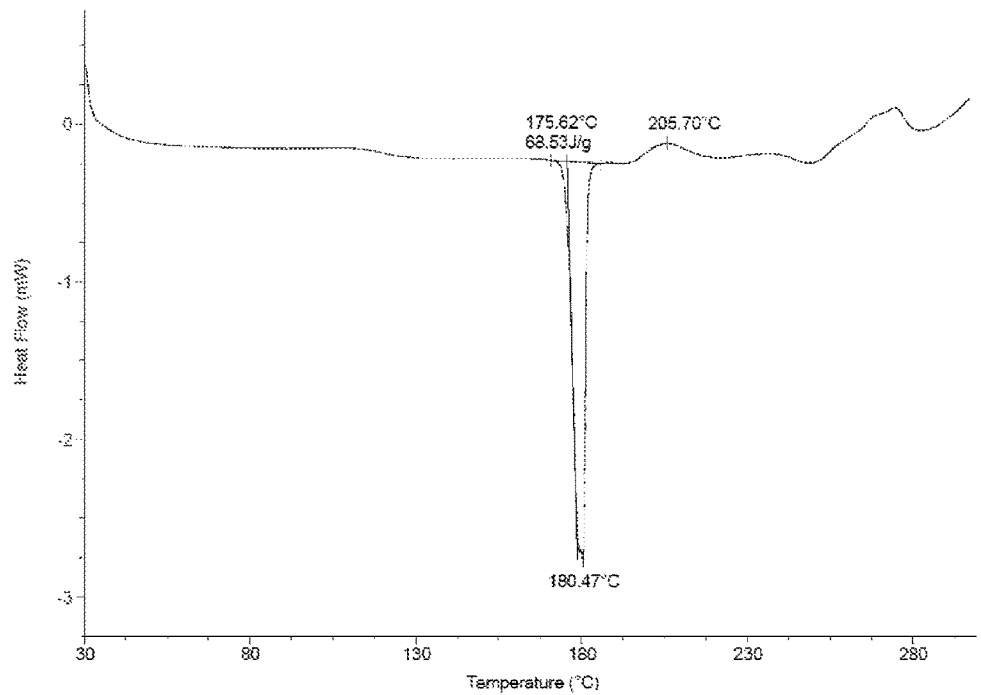
FIG. 2 is the DSC pattern of the crystal form I.

5. The crystal form I according to claim 1, comprising a DSC pattern as shown in FIG. 2.

Figure 3:
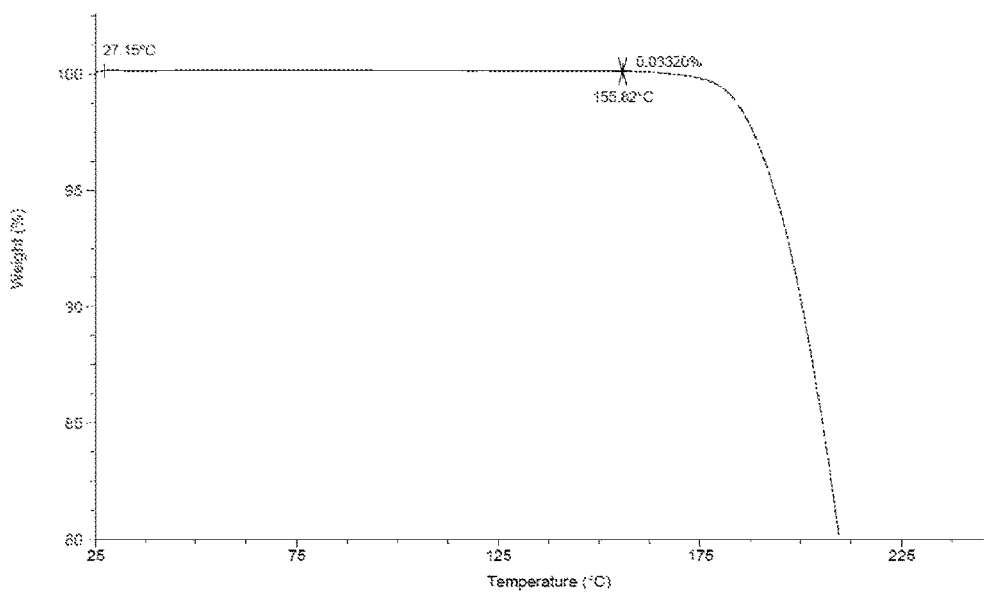
FIG. 3 is the TGA pattern of the crystal form I.

6. The crystal form I according to claim 1, comprising a TGA pattern as shown in FIG. 3.

7. A preparation method of Compound 1, comprising the following steps:

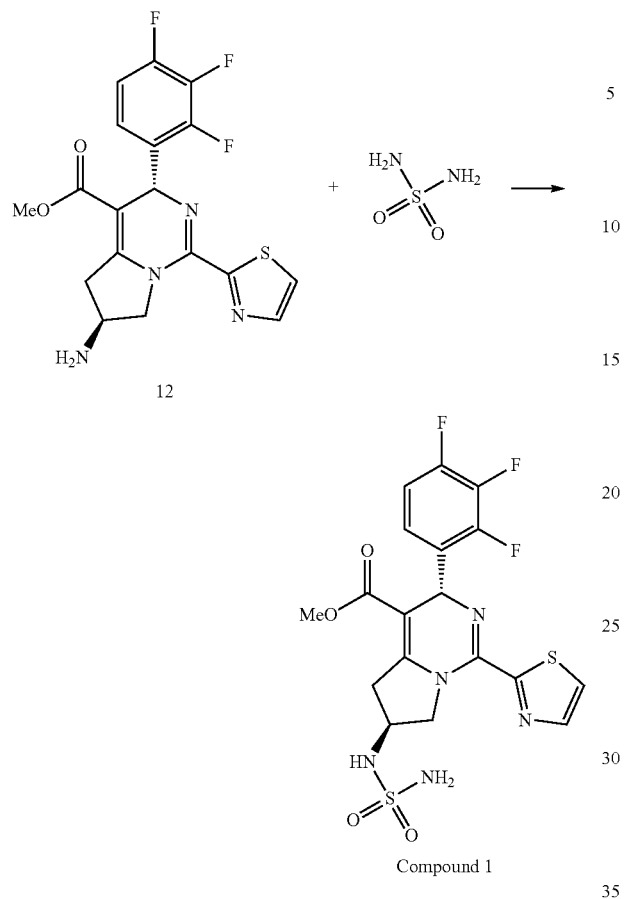

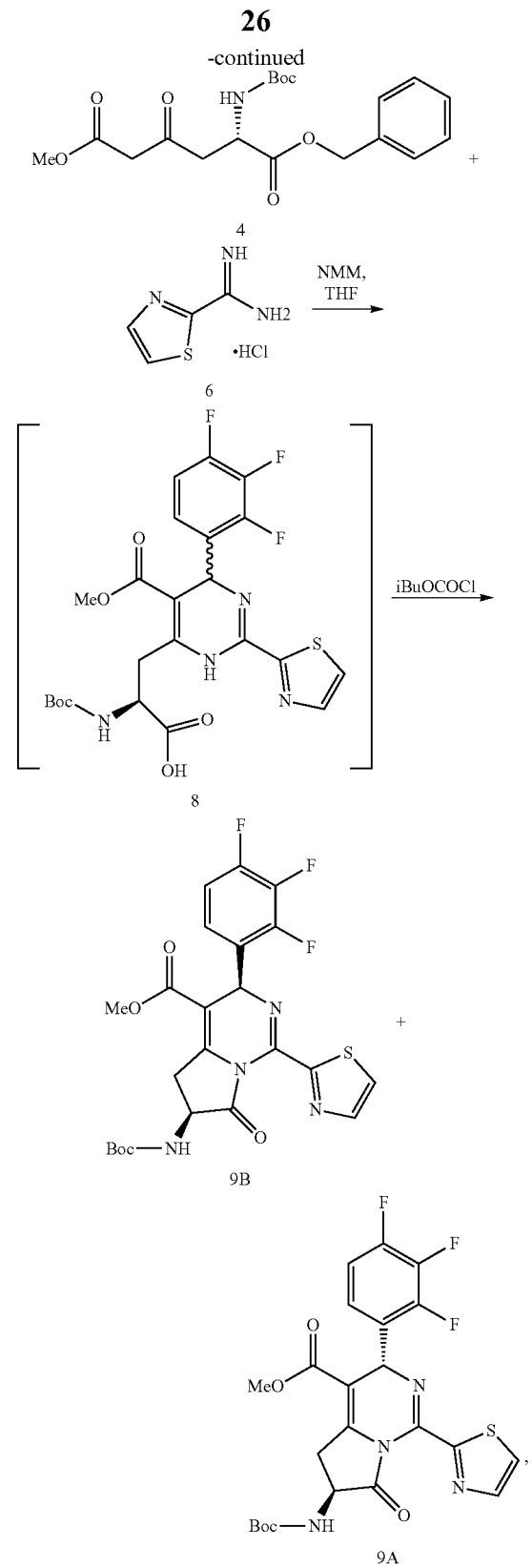

wherein,
the reaction step does not require an addition of an organic base or an inorganic base;
the reaction solvent is selected from 1,4-dioxane or tetrahydrofuran;
the molar ratio of Compound 12 to aminosulfonamide is selected from 1:1-20;
the reaction temperature is selected from 60° C. to reflux temperature;
optionally, Compound 1 is purified by recrystallization in a single solvent or a mixed solvent of several solvents selected from the group consisting of dichloromethane, ethyl acetate, isopropyl acetate, n-heptane, n-hexane, cyclohexane and petroleum ether.

8. The preparation method according to claim 7, comprising the following steps:

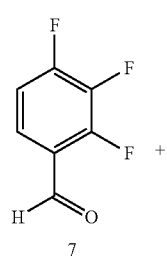

wherein,
the molar ratio of NMM to Compound 4 is 1-4:1;
optionally, Compound 8 is directly added to the next reaction without separation;

optionally, the mixture of Compound 9A and Compound 9B provided by the reaction is separated and purified by recrystallization in a single solvent or a mixed solvent of several solvents selected from the group consisting of ethyl acetate, isopropyl acetate, tetrahydrofuran, dioxane, cyclohexane and n-heptane to give Compound 9A.

9. The preparation method according to claim 7, comprising the following steps:

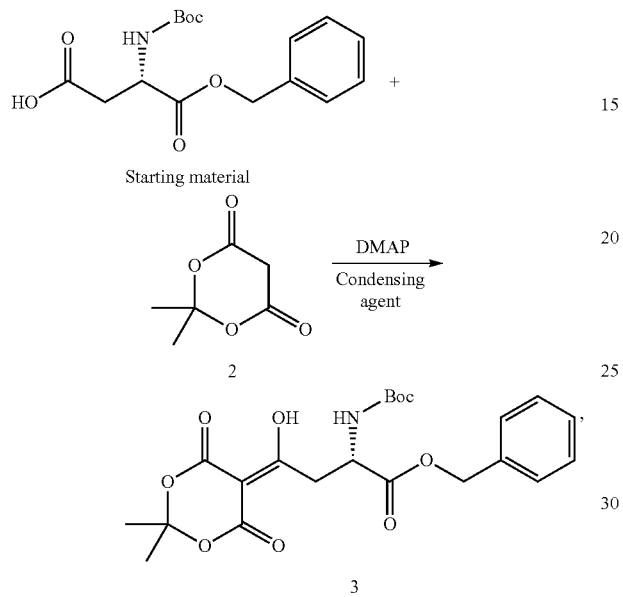

the condensing agent is selected from EDCI, DCC, DIC, DMC, HOBT, HATU, CDI;
the reaction temperature is selected from −20° C. to 10° C.;
optionally, Compound 3 is added directly to the next reaction without separation.

10. The preparation method according to claim 7, comprising the following steps:

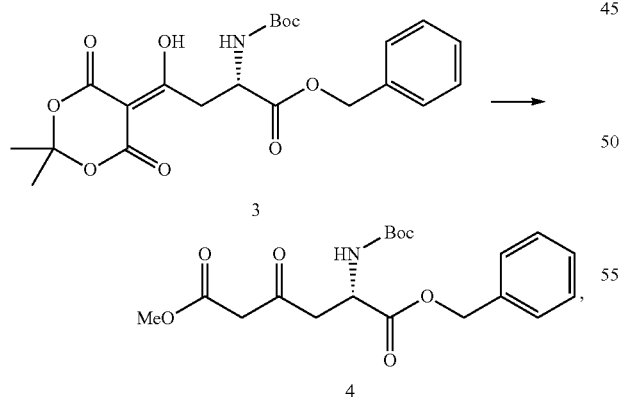

the reaction solvent is a single solvent or a mixed solvent of several solvents selected from the group consisting of methanol, ethanol, isopropanol, n-butanol, t-butanol, tetrahydrofuran, ethyl acetate, toluene and xylene;
optionally, Compound 4 is purified by stirring crystallization, slurrying or recrystallization in a single solvent or a mixed solvent of several solvents selected from the group consisting of methanol, ethanol, isopropanol, n-butanol, cyclohexane, n-hexane, n-heptane and petroleum ether;
Compound 4 is purified by stirring crystallization or slurrying at the temperature of −5° C. to 30° C.

11. The preparation method according to claim 7, comprising the following steps:

-continued
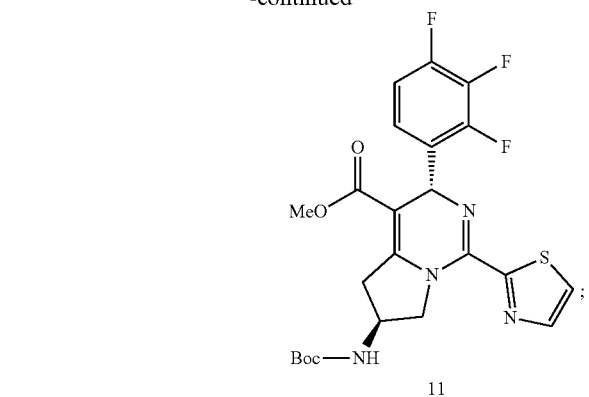
11
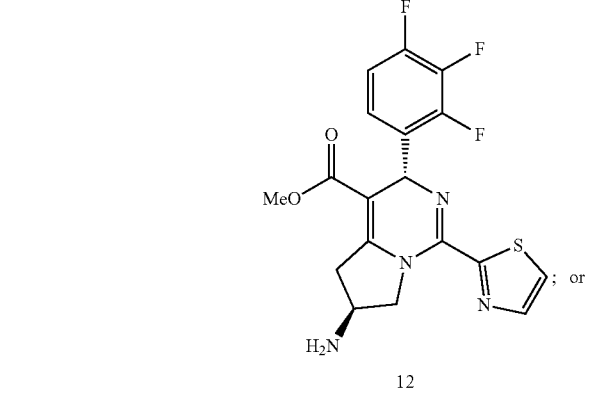
11
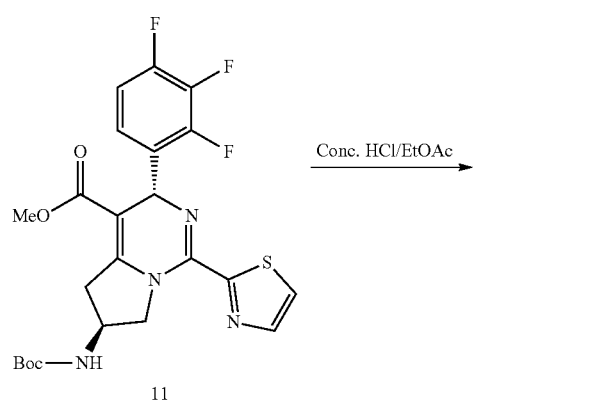
12
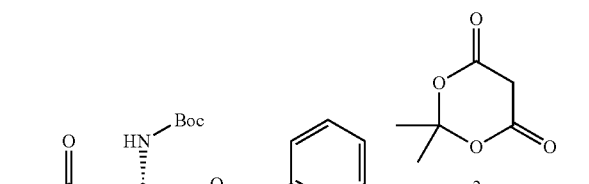
Starting material
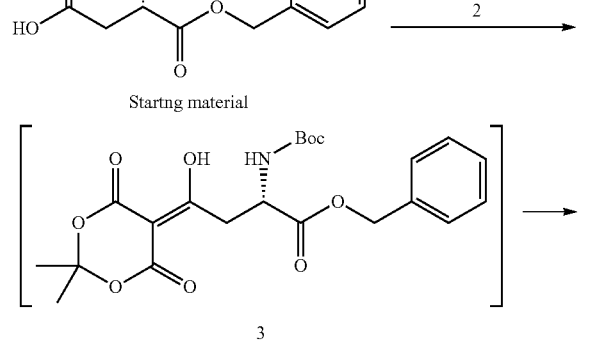
3
-continued
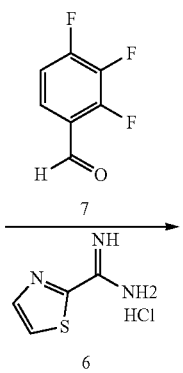
7
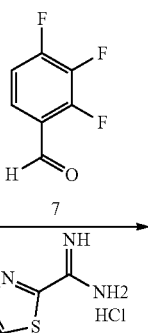
6
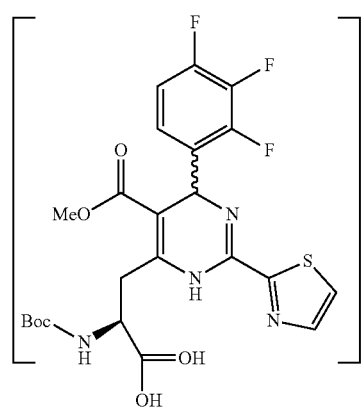
8
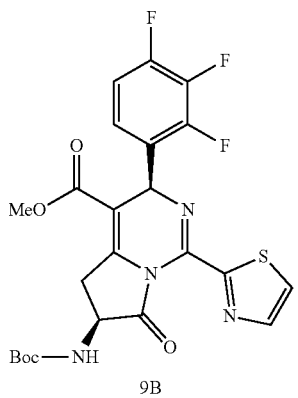
9B
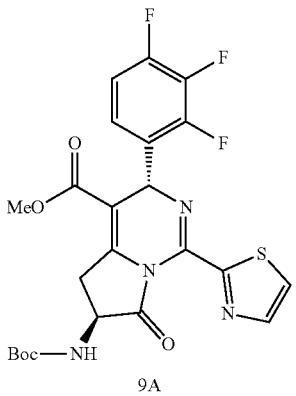
9A

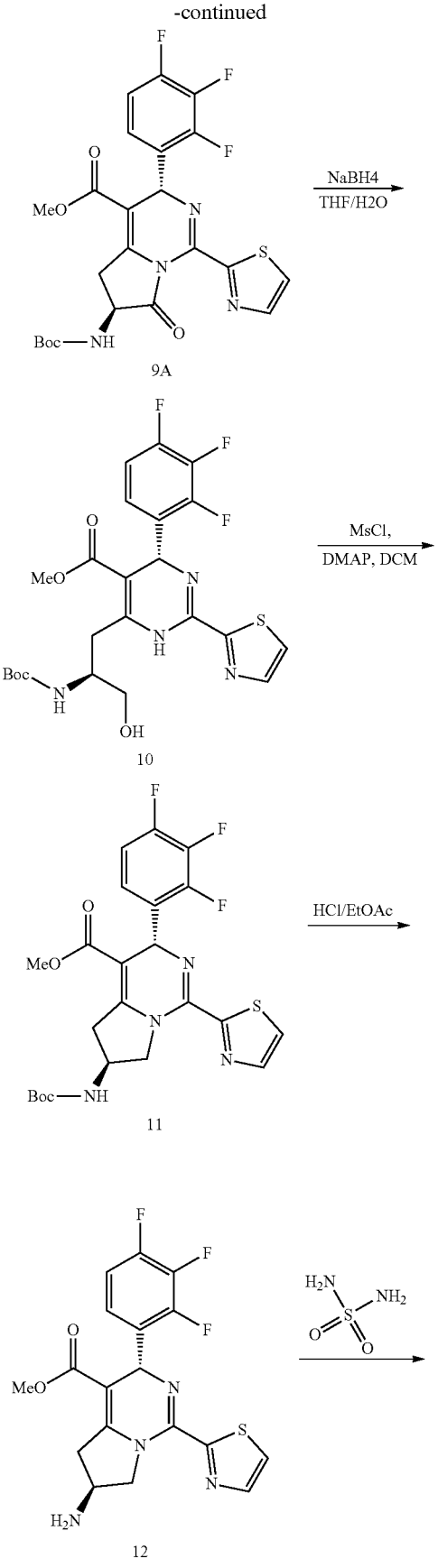
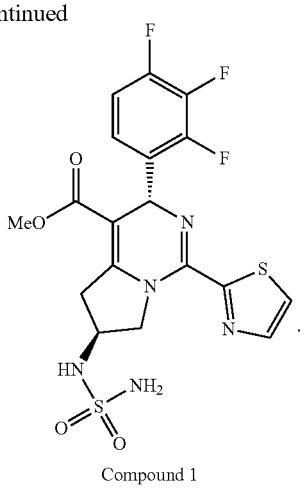

Compound 1

12. The preparation method of the crystal form I of Compound 1 according to claim 4, comprising the following steps: adding Compound 1 to a mixed solvent of ethyl acetate and petroleum ether for recrystallization, wherein the volume ratio of ethyl acetate to petroleum ether is 1:0.5-2; or
adding Compound 1 to ethyl acetate and heating to reflux for dissolution, then dropwise adding n-heptane, and slowly cooling the mixture to 10° C. to −10° C. for crystallization, wherein the volume ratio of ethyl acetate to n-heptane is 1:0.5-2.

13. A medicament for treating HBV-related diseases comprising the crystal form I of Compound 1 according to claim 1.

14. A method of decreasing a level of hepatitis B virus (HBV), the method comprising:
contacting the HBV with the crystal form I of Compound 1 according to claim 1.

15. The preparation method according to claim 7, wherein the molar ratio of Compound 12 to aminosulfonamide is 1:10.

16. The preparation method according to claim 8, wherein the molar ratio of NMM to Compound 4 is 2-3: 1.

17. The preparation method according to claim 8, wherein the recrystallization solvent is selected from a mixed solvent of ethyl acetate, tetrahydrofuran and n-heptane.

18. The preparation method according to claim 17, wherein the volume ratio of n-heptane, ethyl acetate and tetrahydrofuran in the mixed solvent is (6-54):(2-18): 1.

19. The preparation method according to claim 18, wherein the volume ratio of n-heptane, ethyl acetate and tetrahydrofuran in the mixed solvent is 18: 6: 1.

20. The preparation method according to claim 9, wherein the reaction temperature is selected from −10° C. to 0° C.

21. The preparation method according to claim 10, wherein the reaction solvent is a mixed solvent of toluene and methanol.

22. The preparation method according to claim 10, Compound 4 is purified by stirring crystallization or slurrying at the temperature of 10° C. to 20° C.

23. The preparation method according to claim 10, Compound 4 is purified by stirring crystallization, slurrying or recrystallization in a mixed solvent selected from the group consisting of ethanol/cyclohexane, ethanol/n-hexane, ethanol/n-heptane or ethanol/petroleum ether.

24. The preparation method according to claim 23, the volume ratio of ethanol to cyclohexane, n-hexane, n-heptane or petroleum ether in the mixed solvent is selected from 1: 1-3.

25. The preparation method according to claim 23, the mixed solvent is ethanol/petroleum ether, and the volume ratio of ethanol to petroleum ether is 3: 5.

26. The preparation method according to claim 12, comprising the following steps: adding Compound 1 to a mixed solvent of ethyl acetate and petroleum ether for recrystallization, wherein the volume ratio of ethyl acetate to petroleum ether is 1: 1; or adding Compound 1 to ethyl acetate and heating to reflux for dissolution, then dropwise adding n-heptane, and slowly cooling the mixture to 10° C. to −10° C. for crystallization, wherein the volume ratio of ethyl acetate to n-heptane is 1: 1.

* * * * *